United States Patent [19]

Inglis et al.

[11] Patent Number: 5,119,811
[45] Date of Patent: Jun. 9, 1992

[54] TRACHEAL ASSEMBLY HAVING INNER AND OUTER TUBES AND SURFACE MATERIALS

[75] Inventors: Timothy J. J. Inglis, Leeds; Michael R. Millar, Shawford, both of England

[73] Assignee: Smiths Industries Public Limited Company, London, England

[21] Appl. No.: 656,434

[22] Filed: Feb. 19, 1991

[30] Foreign Application Priority Data

Feb. 21, 1990 [GB] United Kingdom ............... 9003857

[51] Int. Cl.$^5$ .................. A61M 16/00; A62B 9/06
[52] U.S. Cl. ............... 128/207.14; 128/200.26; 604/94
[58] Field of Search ............ 128/200.26, 207.14, 128/207.15, 207.16, 207.17, 911, 912, DIG. 26; 604/94, 96, 93, 158, 165, 166, 239, 263, 264, 280, 282

[56] References Cited

U.S. PATENT DOCUMENTS

| | | | |
|---|---|---|---|
| 2,765,792 | 10/1956 | Nichols | 128/200.26 |
| 2,786,469 | 3/1957 | Cohen | 128/200.26 |
| 2,923,299 | 2/1960 | Blackwood | 128/207.14 |
| 3,039,469 | 6/1962 | Fountain | 128/200.26 |
| 3,088,466 | 5/1963 | Nichols | 128/200.26 |
| 3,169,529 | 2/1965 | Koenig | 128/207.14 |
| 3,225,767 | 12/1965 | Smith | 128/200.26 |
| 3,334,631 | 8/1967 | Stebleton | 128/200.26 |
| 3,606,669 | 9/1971 | Kemble | 128/200.26 |
| 4,827,925 | 5/1989 | Vilasi | 128/207.14 |
| 5,024,220 | 6/1991 | Holmgreen et al. | 128/207.14 |

FOREIGN PATENT DOCUMENTS

| | | | |
|---|---|---|---|
| 0037719 | 10/1981 | European Pat. Off. | 128/207.14 |
| 1082749 | 9/1967 | United Kingdom | 128/207.14 |

*Primary Examiner*—Edgar S. Burr
*Assistant Examiner*—Kimberly L. Asher
*Attorney, Agent, or Firm*—Pollock, Vande Sande & Priddy

[57] ABSTRACT

A tracheal tube assembly has an outer tube and an inner cannula with a patient end that is flared outwardly to a diameter greater than the internal diameter of the outer tube. When inserted in the outer tube, the patient end of the inner cannula is deformed inwardly and forms a wiping seal. The remainder of the inner cannula has an external diameter less than the internal diameter of the outer tube so that it is readily inserted. The inner cannula may be coextruded with an outer layer of a low friction material such as a polyolefine.

7 Claims, 1 Drawing Sheet

TRACHEAL ASSEMBLY HAVING INNER AND OUTER TUBES AND SURFACE MATERIALS

BACKGROUND OF THE INVENTION

This invention relates to tracheal tube assemblies and to methods of assisting ventilation.

Tracheal tube assemblies having an outer tube and inner cannula are known. With such assemblies, the inner cannula is removed and replaced periodically when secretions have built up on the cannula to an extent that there is a risk of blockage. Tracheal tube assemblies are described, for example, in U.S. Pat. No. 3948274, GB 2056285B, GB 1099277, GB 125754, WO 90/04992, FR 2539998A, DE 72467, DE 1268313, EP 0107779A, U.S. Pat. No. 4817598, U.S. Pat. Nos. 3659612, 4009720, 3088466, 4315545, 2765792, 3169529, 3263684, 3334631, 3587589, 3688774, 3731692, 3889688, 3948273, 3973569, 3987798, 4033353, 4045058, 4235229, 4471776, 4593690.

The inner surface of tracheal tubes, in use, tends to accumulate a film of respiratory secretions and bacteria. This film can obstruct the bore of the tube and reduce gas flow along it. It has been found that the film can also act as a site for build up of bacteria in quantities sufficient to cause infection if dislodged from the tube and subsequently inhaled. The use of an inner cannula which is periodically removed and replaced, can reduce these effects but brings with it disadvantages. In particular, the thickness of the wall of the inner cannula will itself reduce the effective bore of the tube. This can be mitigated by making the external diameter of the inner cannula as close as possible to the internal diameter of the tube and making the cannula wall as thin as possible in order to maximize the diameter of the gas passage through the tube assembly. It is also important to prevent passage of secretions between the outside of the cannula and the inside of the outer tube. A close fitting inner cannula can, however, be difficult to insert because of friction with the bore of the tube. This can make the inner cannula prone to kinking, especially if the wall of the cannula is thin. This difficulty is aggravated by the fact that the inner cannula is preferably made of material to which secretions will cling without becoming dislodged into the bronchii and that these materials, such as PVC, tend to have a relatively high coefficient of friction. These materials also tend to be relatively flexible, so that the cannula wall must be made thick enough to prevent kinking on insertion.

SUMMARY OF THE INVENTION

It is an object of the present invention to provide an improved tracheal tube assembly.

According to one aspect of the present invention there is provided a tracheal tube assembly of the kind having an outer tube and an inner cannula that is insertable within and removable from the outer tube, the inner cannula having at its patient end an external diameter that is greater than that of the major part of the inner cannula, the external diameter at the patient end being at least equal to the internal diameter of the outer tube such that the inner cannula seals with the outer tube at its patient end, and the external diameter of the major part of the inner cannula being less than the internal diameter of the outer tube so that the inner cannula is freely insertable along the outer tube.

The patient end of the inner cannula is preferably deformable radially, before insertion in the outer tube the external diameter of the patient end of the inner cannula being greater than the internal diameter of the outer tube. The inner cannula is preferably flared outwardly at the patient end and may be of a plastic material. The inner cannula may have an inner surface to which respiratory secretions will cling and an outer surface of a different material with a lower coefficient of friction than the inner surface. The inner surface may be of PVC and the outer surface of polyolefine. The patient end of both the inner cannula and the outer tube may be bevelled.

According to another aspect of the present invention there is provided a method of assisting ventilation of a patient comprising the steps of: inserting into the trachea of a patient a tracheal tube assembly of the kind having an outer tube and an inner cannula that is insertable within and removable from the outer tube; removing the inner cannula from the outer tube without removing the outer tube not more than 12 hours after insertion of the assembly such as to remove any respiratory secretions and bacteria that may have accumulated on the inner cannula before they become dislodged but before there has been sufficient accumulation of material in the inner cannula substantially to impede breathing; and inserting a fresh inner cannula into the outer cannula.

The inner cannula is preferably replaced at about six hour intervals.

An endotracheal tube assembly in accordance with the present invention, will now be described, by way of example, with reference to the accompanying drawings.

DETAILED DESCRIPTION OF PREFERRED EMBODIMENT

Figure 1:
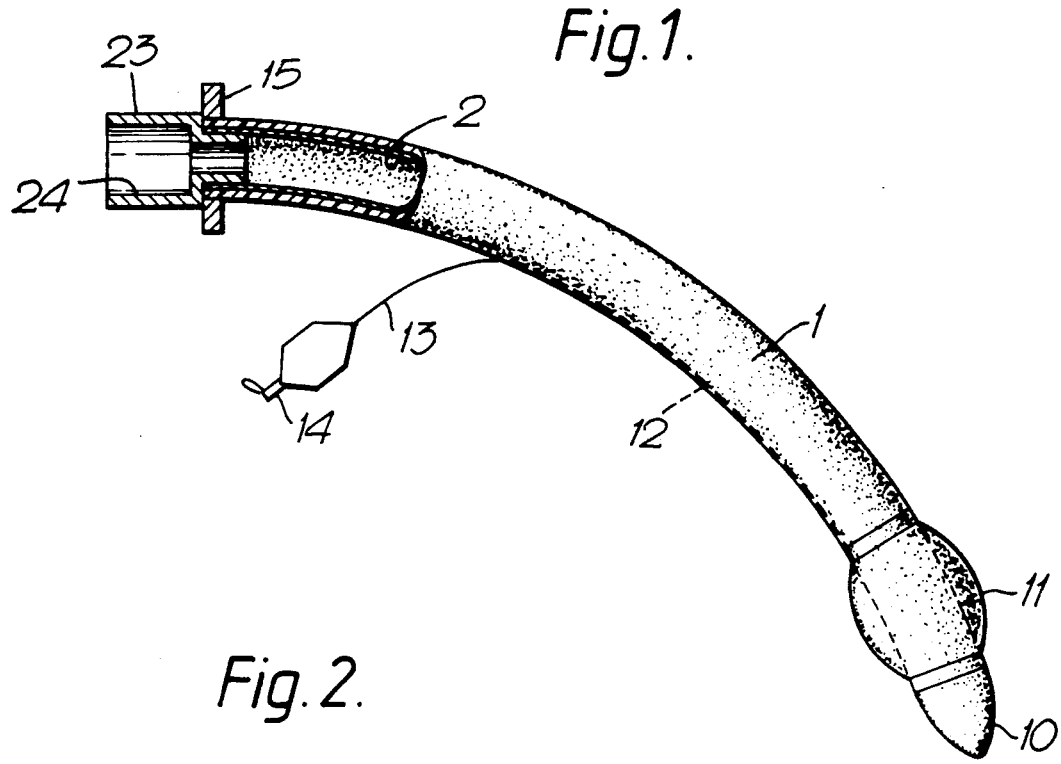
FIG. 1 is a sectional side elevation of a part of the assembly.
Figure 2:
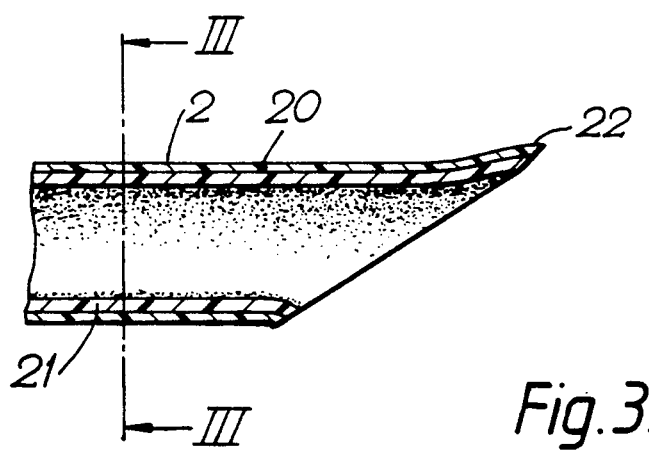
FIG. 2 is an enlarged side elevation section of a part of the assembly.
Figure 3:
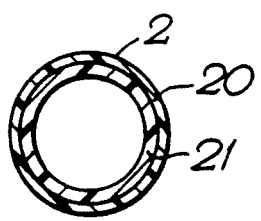
FIG. 3 is a transverse sectional view along the line III—III of FIG. 2.

The assembly comprises an outer endotracheal tube 1 of conventional construction and an inner cannula 2 which is insertable in, and removable from, the outer tube.

The outer tube 1 is of a constant radius curvature along its length and is made of PVC or a similar plastics material. At its forward, patient end, the tube 1 has a bevelled, open tip 10 which, in use, is located in the trachea of the patient. Close to the forward end, a cuff 11 embraces the tube which is inflatable via a lumen 12 extending along the wall of the tube which communicates with an inflation line 13 and connector 14. A flange 15 is connected to the rear, machine end of tube 1 where it emerges from the mouth of the patient.

The inner cannula 2 is of the same length as the outer tube 1 and in preformed with the same curvature. The inner cannula 2 is a coextrusion of two different materials. More particularly, the outer layer 20 is of a relatively low friction plastics material such as a polyolefine, for example, a low density polyethylene or polypropylene. The inner layer 21 is of a material with a higher coefficient of friction but which enables respiratory secretions and bacteria to cling to it. In this respect, the inner layer 21 may be of the same material as the outer tube 1, namely PVC. Various different factors determine the degree to which secretions will cling to the inner layer 21. For example, a highly polar material will improve adhesion as will the presence of microscopic surface formations. A hydrophilic material may also provide a better site for adhesion of the secretions.

The outer layer 20 is more rigid that the inner layer 21 which is relatively flexible.

The inner cannula 2 is of circular cross-section and of the same external diameter along the major part of its length, which is slightly less than the internal diameter of the outer tube 1. The clearance between the inner cannula and the outer tube is sufficient to enable the inner cannula to be freely inserted and removed without substantially reducing the internal diameter and hence the gas passage through the assembly. Insertion is further facilitated by the low friction outer surface 20 of the cannula.

At its patient end, the cannula 2 is flared outwardly to form a portion 22 which, in its natural state, before insertion in the outer tube 1, has an external diameter slightly greater than the internal diameter of the outer tube.

At its machine end, the cannula 2 has a coupling 23, the forward end of which mates with the machine end of the outer tube 1. The rear end of the coupling is provided with a female luer tapered recess 24 that is adapted to receive a cooperating coupling (not shown) connected to a patient ventilator.

In use, the forward end of the inner cannula 2 is pushed into the machine end of the outer tube 1, the bevel at the forward end of the cannula serving to aid initial insertion into the tube. The deformable nature of the inner cannula allows its forward portion 22 to be deformed inwardly by contact with the inside of the tube. In this way, the portion 22 forms a sliding, wiping seal with the tube 1 as it is pushed along it. The friction produced by contact of the portion 22 with the tube 1 is relatively small because of the small area of contact, so that there is little impediment to insertion. When fully inserted, the forward portion 22 of the inner cannula is a close, sealing fit with the bore of the tube 1 at its patient end. In this way, there is little risk of secretions passing between the inner cannula 2 and the outer tube 1.

The nature of the inner surface 21 of the cannula 2 is such that respiratory secretions and bacteria will readily cling to it with only a low risk of dislodgement.

The inner cannula 2 is periodically removed, when accumulated secretions have built up, and replaced by a new cannula, without the need to remove the outer tube. The inner cannula 2 is removed at least once every twelve hours and preferably more frequently, such as every six hours. Conveniently, the cannula is replaced once every time there is a change in shift of nursing staff. Previously, inner cannulae have been replaced only when secretions have reached the stage of threatening to block passage through the assembly, such as, once a day, or every other day. The importance of more frequent replacement in reduced bacterial infection has not heretofore been appreciated.

Because the outer layer 20 of the inner cannula 2 is of a more rigid material than the inner layer 21, it enables the cannula to be made with a thinner wall than would be possible if it were made entirely from the material of the inner layer, and without the risk of the cannula kinking on insertion.

It will be appreciated that the inner cannula 2 need not be a coextrusion but that the inner or outer surface could be provided by treating or coating with a different material. The assembly could be a tracheostomy tube assembly instead of an endotracheal tube assembly.

What we claim is:

1. In a tracheal tube assembly of the kind having an outer tube and an inner cannula that is insertable within and removable from the outer tube, the improvement wherein the inner cannula is flared outwardly at its patient end so that the patient end of the inner cannula has an external diameter that is greater than that of the major part of the inner cannula, the external diameter at said patient end being at least equal to the internal diameter of the outer tube such that the inner cannula seals with the outer tube at its patient end, and the external diameter of the major part of the inner cannula being less than the internal diameter of the outer tube so that the inner cannula is freely insertable along the outer tube.

2. A tracheal tube assembly according to claim 1, wherein the patient end of the inner cannula is deformable radially, and wherein before insertion in the outer tube the external diameter of the patient end of the inner cannula is greater than the internal diameter of the outer tube.

3. A tracheal tube assembly according to claim 1, wherein the inner cannula is of a plastics material.

4. A tracheal tube assembly according to claim 1, wherein the patient end of both the inner cannula and the outer tube are bevelled.

5. In a tracheal tube assembly of the kind having an outer tube and an inner cannula that is insertable within and removable from the outer tube, the improvement wherein the inner cannula has at its patient end an external diameter that is greater than that of the major part of the inner cannula, the external diameter at said patient end being at least equal to the internal diameter of the outer tube such that the inner cannula seals with the outer tube at its patient end, the external diameter of the major part of the inner cannula being less than the internal diameter of the outer tube so that the inner cannula is freely insertable along the outer tube, the inner cannula having an inner surface to which respiratory secretions will cling and an outer surface of a different material with a lower coefficient of friction than said inner surface.

6. A tracheal tube assembly according to claim 5, wherein the inner surface is of PVC.

7. A tracheal tube assembly according to claim 5, wherein the outer surface is of a polyolefine.

* * * * *